United States Patent [19]

Aussenegg et al.

[11] Patent Number: 5,611,998
[45] Date of Patent: Mar. 18, 1997

[54] OPTOCHEMICAL SENSOR AND METHOD FOR PRODUCTION

[75] Inventors: Franz Aussenegg; Harald Brunner; Alfred Leitner, all of Graz; Fritz Pittner, Vienna; Thomas Schalkhammer, Kasten, all of Austria

[73] Assignee: AVL Medical Instruments AG, Schaffhausen, Switzerland

[21] Appl. No.: 419,615

[22] Filed: Apr. 10, 1995

[30] Foreign Application Priority Data

Apr. 12, 1994 [AT] Austria ........................ 753/94

[51] Int. Cl.⁶ .................................................. G01N 21/75
[52] U.S. Cl. ............................. 422/82.05; 422/82.09; 356/234
[58] Field of Search ............... 250/227.18, 227.14; 356/234; 422/82.05, 82.09

[56]  References Cited

U.S. PATENT DOCUMENTS

| | | | |
|---|---|---|---|
| 4,749,856 | 6/1988 | Walker et al. | 250/227 |
| 4,764,343 | 8/1988 | Nyberg | 422/83 |
| 5,015,843 | 5/1991 | Seitz et al. | 250/227.21 |
| 5,023,053 | 6/1991 | Finlan | 422/82.05 |
| 5,449,918 | 9/1995 | Krull et al. | 250/458.1 |

FOREIGN PATENT DOCUMENTS

| | | |
|---|---|---|
| 5142085 | 6/1993 | Japan . |
| 6222006 | 8/1994 | Japan . |

*Primary Examiner*—Jeffrey Snay
*Attorney, Agent, or Firm*—Watson Cole Stevens Davis, P.L.L.C.

[57]  ABSTRACT

An optochemical sensor for measuring concentrations of analytes is provided with a reactive matrix preferably made of polymeric material capable of swelling. Further provided are a mirror layer and a layer of a plurality of discrete islands that are electrically conductive, between which layers the reactive matrix is positioned, the diameter of the islands being smaller than the wavelength of the light employed for monitoring and evaluation.

21 Claims, 3 Drawing Sheets 4,4'-Diazidostilbene-2,2'-disulfonic acid   Nitrene   Polyvinylpyrrolidone photocrosslinked PVP

OPTOCHEMICAL SENSOR AND METHOD FOR PRODUCTION

BACKGROUND OF THE INVENTION

This invention relates to an optochemical sensor for measuring concentrations of substances by means of a reactive sensor film, and a method for preparing such an optochemical sensor.

Optochemical sensors are based on the fact that a chemical reaction between the sensor material and the analyte leads to a change in the optical properties of the sensor. Such a change may involve optical properties such as absorption or fluorescence, in which instance the reaction may be detected by means of spectroscopic methods.

Optochemical sensors for measuring concentrations of chemical species are met with growing interest for several reasons; compared to conventional measuring devices they are characterized by much shorter response times, greater mechanical robustness, and insensitivity to electromagnetic interferences in addition to other advantages. To ensure a short response time, however, it is essential for such optochemical sensors that the sensor material be sufficiently exposed to the attack of the analyte.

SUMMARY OF THE INVENTION

It is an object of the invention to provide an optochemical sensor of the above kind, which will permit a concentration of an analyte, such as pH value or ionic strength, to be determined in a simple and reproducible manner, where no electrodes are needed and the result of the measurement can be obtained rapidly and most accurately, even if the changes in the concentration to be measured are very small.

In the invention this object is achieved by proposing that the optochemical sensor comprise a mirror layer, a reactive matrix, in particular of material that is capable of swelling, and a film consisting of a plurality of islands of electrically conductive material, especially metal, the diameter of the islands being smaller than the wavelength of the light used for monitoring and evaluation. Such a sensor utilizes the sensor material's property of reversibly changing its volume with the particular chemical environment it is exposed to, i.e., its capacity of swelling or shrinking. In the optochemical sensor of the invention such swelling or shrinking will cause a change in optical thickness between mirror and island film; by configuring the outer layer as a film of discrete islands, the reactive matrix made of swellable material is fully exposed to the attack of the analyte. After a relatively short response time swelling or shrinking of the matrix may be observed. It has come as a surprise that in this kind of structure a change in optical thickness of the matrix is accompanied by a typical change in color. As with all other sensors, the response time of this sensor is determined by the time it takes the substance to be measured to diffuse into the sensor material; by using extremely thin layers or films as proposed by the invention a correspondingly short diffusion path is obtained. With conventional interferometric methods it is hardly possible, however, to detect small changes in the thickness of thin layers. It has been found unexpectedly that in the instance of the matrix being positioned between a mirror and an island film, the solution to be measured is given full access to the matrix, the anomalous optical behavior of the island film provoking a typical color change as an additional advantage. Metallic island films with an island diameter smaller than the wavelength of the light used for monitoring and evaluation are characterized by strong absorption, as a consequence of which the film structure described above is characterized by strong narrow-band reflection minima whose spectral positions are extremely sensitive to and dependent on the thickness of the transparent intermediate layer. Even minute changes of an extremely thin intermediate layer will lead to an extremely strong spectral shift of the reflection minimum, so that changes in concentration can be detected easily after a very short response time due to the extreme thin-wall structure.

In a preferred embodiment wherein the mirror layer is metallic, the metal chosen for mirror and island film should be gold. Basically it would be possible to use other metals, such as aluminum or silver, for preparation of the mirror and the island film. Such other metals are more sensitive to chemical attack, however, than the island film of gold preferred by the invention. In addition, gold is characterized by excellent absorption properties and thus a high sensitivity and strong spectral shift of the reflection minima.

The mirror layer could also be non-metallic, however, in which instance it is preferred that the Fresnel reflection occurring at the polymer/air interface be utilized as mirror.

A particularly strong spectral shift is observed if the islands have a diameter that is appreciably smaller than the wavelength of the light used for monitoring and evaluation. In a preferred embodiment the diameter of the islands is smaller than 100 nm, in particular, smaller than 60 nm, if visible light is used for evaluation.

Preferred materials for the reactive matrix capable of swelling are optically transparent polymers, such as polyacrylic acid derivatives or polyvinylpyrrolidone derivatives, i.e., especially acrylic acid-acrylamide copolymers. Such polymers are characterized by selective swelling or shrinking following a change in ionic strength or concentration of the substance to be measured.

It will suffice in this case if such a sensor is brought into contact with a solution whose concentration is to be determined.

Due to the thin film and short response time, and the clearly visible strong spectral shift of the reflection minima, a change in color can be detected rapidly and reliably. At the same time, the relatively simple design of the optochemical sensor will give a high degree of mechanical stability. To ensure sufficiently short response times and distinct spectral shifts of the reflection minimum of the film structure, it is proposed in a preferred embodiment that the optical thickness of the polymer matrix be less than 1,000 nm, in particular, less than 600 nm. To increase the rate of response the optical thickness may be less than 100 nm; in principle, film thicknesses of slightly greater than 10 nm to 15 nm are possible if suitable polymers are selected.

In order to maintain the high absorption desired by the invention along with good permeability for the diffusion of the analyte, the island film should have a mass thickness of less than 20 nm, i.e., preferably less than 15 nm, its light absorption preferably amounting to 40–60 percent for the particular wavelength used, to ensure a particularly high sensitivity.

The optochemical sensor described by the invention can be prepared in a simple manner, by vapor-depositing the island film on the polymer matrix, or rather, on the metal layer and the polymer layer. By means of this technique of vapor deposition the extremely small mass thickness and the formation of discrete islands required by the invention may be obtained, which will produce the typical strong spectral shift of the reflection minima. As an alternative, the island film may be prepared or modified by the attachment of metallic particles or islands to the polymer matrix, or by removing excess metal from the polymer film, thereby producing islands or changing their number or size, in which way the desired mass thickness may be accurately obtained.

To extend the field of applications for optochemical sensors according to the invention, a preferred method provides that enzymes or catalysts be immobilized in the polymer matrix. In this way the concentration of a species produced by an enzymatic reaction or catalytic conversion can be determined immediately and in situ, opening up a number of new and interesting applications. Another preferred method of preparing a polymer matrix proposes that polyvinylpyrrolidone with a molecular weight of 280,000 to 2,000,000 be cross-linked with a bisazide, such as Na-4,4'-diacidostilbene-2,2'-disulphonate-tetrahydrate, or 2,6-bis-(4-acidobenzylidene-methylcyclohexanone), and cured by ultraviolet radiation.

As mentioned before, the main feature of an optochemical sensor according to the invention is its extreme thin-wall structure, which will permit much higher response rates and shorter response times. The typical optical indication largely depends on the anomalous absorption behavior of island films, in particular, a broad-band absorption in the visible range; such behavior is explained by the fact that the mobility of electrons is limited in particles of nanometric size. In the instance of unlimited mobility in larger-size particles, as is the rule with continuous metal films, a strong unspecific reflectivity is usually observed, which is also known as metallic lustre. In principle, a special form of reflection interference filter is obtained by the invention, in which an island film of anomalous absorption behavior is used as one of the two reflecting layers, which will lead to a substantially different optical behavior.

Basically, the use of different optical densities and different wavelengths will serve to find an optimum response rate for the measurement of certain analytes. Tests have shown that color changes can be reliably detected for visual discrimination between different thicknesses in increments of some 10 to 30 nm change in optical thickness; this change in optical thickness is due to a change in ionic strength and ensuing swelling of the polymer matrix, and may be calibrated in a simple way. It has been found especially that sulphonic acid groups in a polymer may cause shrinking at high ionic strength, and that these processes are fully reversible if a chemical environment is maintained that does not destroy the matrix or the island film.

The change in the degree of swelling of a ionic polymer upon a change in pH can also be induced by a preceding biochemical reaction: If urea is separated by means of urease, for example, a shift in pH is observed due to the formation of NH3; if glucose is released by means of glucose oxidase, a pH shift takes place due to the occurrence of gluconic acid; if organic esters are released by lipases or esterases, a change in pH is caused by free organic acid. All of the above changes in pH may be utilized in situ and immediately at the sensor for a change in thickness, and thus an optical indication.

Suitable polymer materials capable of swelling include not only ionic derivatives of polyacrylic acid but also enzyme substrates lending themselves to photo-structurization, such as polyvinyl- pyrrolidones that are photo-crosslinked with bisazides, especially for use with enzymes, which may be immobilized in such polymer substrates in a simple manner.

Finally, microcolloidal particles may also be attached to the vapor-deposited metal islands, where they will lead to concentration-dependent and reversible optical changes. In addition to reversible applications of the optical sensor other uses are of interest where the optochemical sensor cannot be employed more than once. Such optochemical sensors may exploit reactions leading to the chemical destruction of the metal island structures: islands of gold, for example, may dissolve into a corrosive gold solution as a consequence of in-situ development of hydrogen peroxide caused by oxidase enzymes, and a reaction with potassium iodide or sodium cyanide. Furthermore, glucose, glutamate, lactate, etc. may lead to chemical destruction of the structure due to a direct reaction between the analyte and the enzyme, making them suitable for use with one-way sensors.

BRIEF DESCRIPTION OF THE DRAWINGS

The invention will be further described with reference to the accompanying drawings in which.

DETAILED DESCRIPTION OF A PREFERRED EMBODIMENTS

Figure 1:
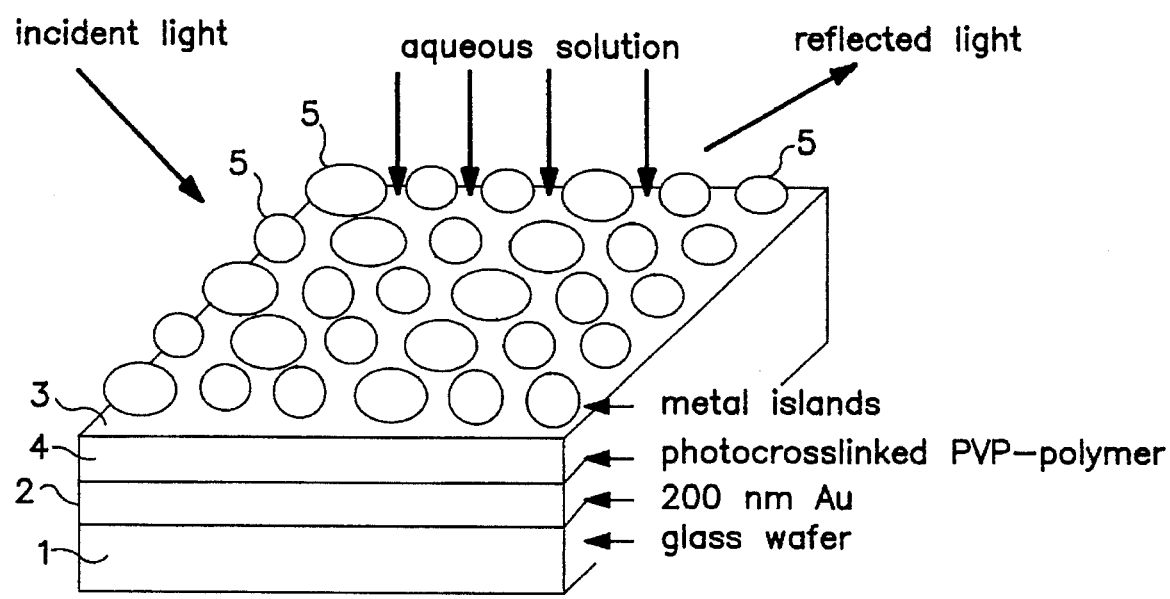
FIG. 1 is a schematic illustration of the inventive optochemical sensor.
Figure 2:
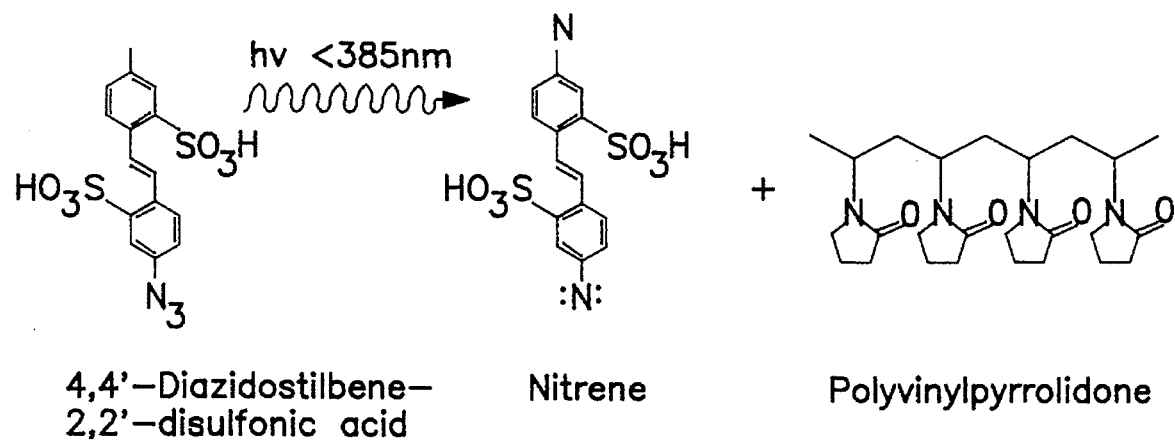
FIG. 2 is an example for a reactive matrix material for inventive sensor.
Figure 2:
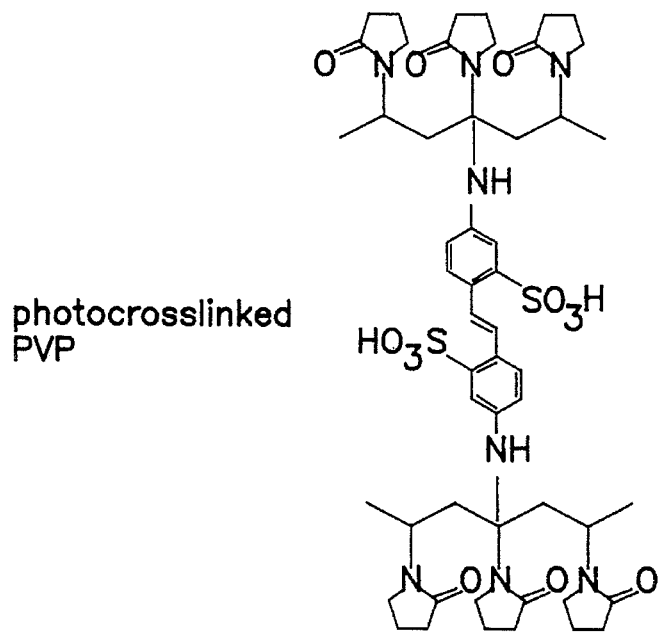

The optochemical sensor of FIG. 1 embodiment comprises a substrate layer 1, e.g., made of a glass wafer and a 200 nm gold coating as a mirror layer 2. Between the mirror layer 2 and a film 3 consisting of a plurality of islands 5 of electrically conductive material a reactive matrix layer 4 is situated. The matrix layer 4 is made of a material that is capable of swelling. The reactive matrix layer 4 can be derived, e.g., via crosslinking reaction of polyvinylpyrrolidone with 4,4'-diazidostilbene-2,2'-disulfonic acid as shown in FIG. 2.

Figure 3:
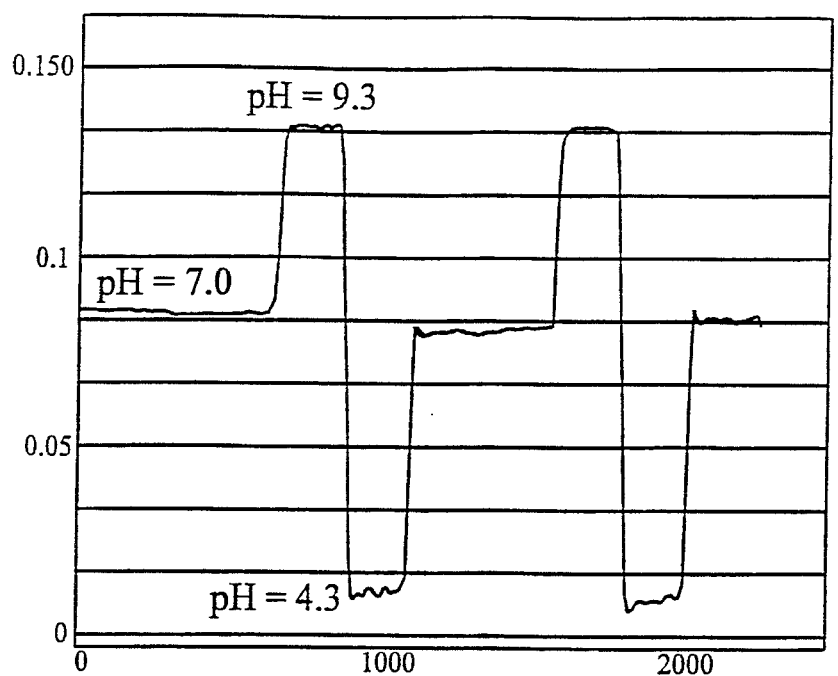
FIG. 3 is a graph showing the influence of pH on polymer swelling and shrinking, and FIG. 4 a time graph of a stability test by reversible pH induced swelling and shrinking.

FIG. 3 shows the influence of pH on polymer swelling and shrinking using $Na_2HPO_4/NaH_2PO_4$ buffer (200 mM) over the pH 4.3 to 9.3 range.

Figure 4:
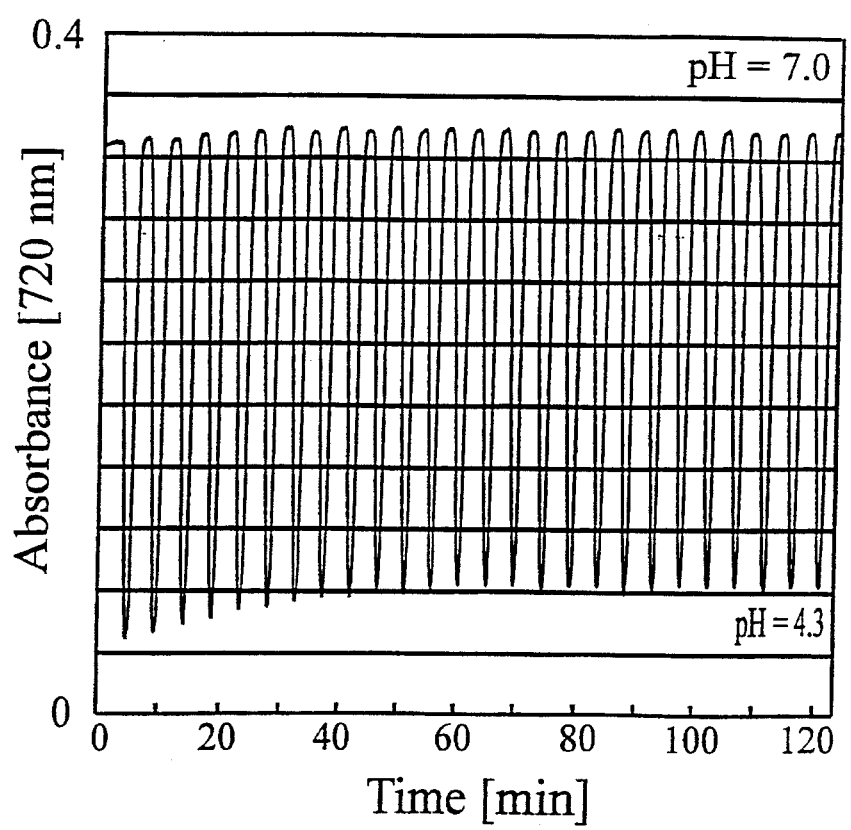

FIG. 4 shows the absorbance of such a sensor at a wavelength of 720 nm due to pH induced swelling and shrinking of the reactive matrix layer over the pH 4.3 to 7.0 range.

We claim:

1. Optochemical sensor system for measuring the concentration of a substance, said system comprising a light source and a sensor, said light source emitting incident light at a wavelength toward said sensor for irradiating said sensor, said sensor comprising:

a mirror layer, an island layer consisting of a plurality of islands of electrically conductive material, said islands having a diameter smaller than the wavelength of incident light emitted from said light source and used for irradiating said sensor, and a reactive matrix situated between said mirror layer and said island layer, said reactive matrix being composed of a material which is capable of swelling or shrinking in the presence of the substance to be measured depending on the concentration of the substance, wherein the shrinking or swelling of the reactive matrix causes a change in color of light reflected from said sensor, wherein the change of color can be monitored as an optical response due to swelling or shrinking of said reactive matrix.

2. Optochemical sensor system according to claim 1, wherein said islands of said island layer are made of metal.

3. Optochemical sensor system according to claim 1, wherein said mirror layer and said islands of said island layer are made of gold.

4. Optochemical sensor system according to claim 1, wherein said island layer has a mass thickness of less than 20 nm.

5. Optochemical sensor system according to claim 1, wherein said island layer has a light absorption of 40–60 percent for the particular wavelength used.

6. Optochemical sensor system according to claim 1, wherein said mirror layer is formed as a second island layer consisting of a second plurality of islands of electrically conductive material, said islands of said second island layer having a diameter which is smaller than the wavelength of incident light emitted from said light source and used for irradiating said sensor.

7. Optchemical sensor system according to claim 1, wherein said wavelength is in the visible light region and the diameter of said islands is smaller than 100 nm.

8. Optochemical sensor system according to claim 7, wherein the diameter of said islands is smaller than 60 nm.

9. Optochemical sensor system according to claim 1, wherein said reactive matrix comprises an optically transparent polymer selected from the group consisting of polyacrylic acid derivatives and polyvinylpyrrolidone derivatives.

10. Optochemical sensor system according to claim 9, wherein said reactive matrix is an acrylic acid acrylamide copolymer.

11. Optochemical sensor system according to claim 1, wherein the optical thickness of said reactive matrix is less than 1,000 nm.

12. Optochemical sensor system according to claim 11, wherein the optical thickness of said reactive matrix is less than 100 nm and said wavelength is in the visible light region.

13. Optochemical sensor system for measuring the concentration of a substance, said system comprising a light source and a sensor, said light source emitting incident light at a wavelength toward said sensor for irradiating said sensor, said sensor comprising:

a mirror layer, an island layer consisting of a plurality of islands of electrically conductive material, said islands having a diameter smaller than the wavelength of incident light emitted from said light source and used for irradiating said sensor, and a matrix situated between said mirror layer and said island layer, wherein said island layer undergoes chemical destruction due to reaction processes with the substance to be measured or with reaction products of the substance depending on the concentration of the substance to be measured, wherein the chemical destruction of said island layer causes a change in color of light reflected from said sensor, wherein the change of color can be monitored as an optical response due to chemical destruction of said island layer.

14. Optochemical sensor system according to claim 13, wherein said mirror layer is formed as a second island layer consisting of a second plurality of islands of electrically conductive material, said islands of said second island layer having a diameter which is smaller than the wavelength of incident light emitted from said light source and used for irradiating said sensor.

15. Method for preparing an optochemical sensor system for measuring the concentration of a substance, said method comprising the steps of:

a) providing a light source which emits incident light at a wavelength;

b) providing a substrate layer;

c) applying a mirror layer to said substrate layer;

d) applying a reactive matrix layer to said mirror layer, said reactive matrix layer being composed of a material which is capable of swelling or shrinking in the presence of said substance to be measured depending on the concentration of the substance to be measured, wherein the shrinking or swelling of the reactive matrix causes a change in color of light reflected therefrom; and e) applying an island layer to said reactive matrix layer, said island layer having islands with a diameter smaller than the wavelength of incident light emitted from said light source.

16. Method according to claim 15, wherein the island layer is vapor-deposited on said reactive polymer matrix in step e).

17. Method according to claim 15, wherein said island layer is prepared or modified by the attachment of metallic particles or islands to said reactive matrix in step e).

18. Method according to claim 15, wherein the islands of said island layer are produced, or their number or size is changed, by removing excess metal from said reactive polymer matrix.

19. Method according to claim 15, wherein enzymes or catalysts are immobilized in said reactive matrix.

20. Method according to claim 15 wherein polyvinylpyrrolidone with a molecular weight of 280,000 to 2,000,000 is cross-linked with bisazides belonging to a group consisting of Na-4,4'-diacidostilbene-2,2'-disulphonatetetrahydrate, and 2,6-bis-(4-acidobenzylidenemethylcyclohexanone), and cured by ultraviolet radiation, in order to prepare said reactive polymer matrix of step d).

21. Optochemical sensor system for measuring the concentration of a substance, said system comprising a light source and an optochemical sensor, said light source emitting incident light at a wavelength toward said sensor for irradiating said sensor, said sensor comprising:

an island layer consisting of a plurality of islands of electrically conductive material, said islands having a diameter smaller than the wavelength of incident light emitted from said light source, and a reactive matrix situated on one side of said island layer, said reactive matrix being composed of a material which is capable of swelling or shrinking in the presence of the substance to be measured depending on the concentration of the substance, wherein shrinking or swelling of the reactive matrix causes a change in color of light reflecting from said sensor, wherein the change of color can be monitored as an optical response due to swelling or shrinking of said reactive matrix, and wherein said reactive matrix includes a first surface adjacent said island layer and a second surface opposite said first surface and which forms an interface with ambient air, said second surface providing a mirror layer realized by Fresnel reflection occurring at said interface.

\* \* \* \* \*